United States Patent [19]
Neubauer et al.

[11] Patent Number: 6,129,752
[45] Date of Patent: Oct. 10, 2000

[54] DISTAL END DEVICE FOR AN IMPLANTABLE ELECTRICAL CONDUCTOR AND AN ELECTRICAL CONDUCTOR EQUIPPED WITH SUCH AN END DEVICE

[75] Inventors: Heinz Neubauer, Järfälla; Ulf Lindegren, Enskede, both of Sweden

[73] Assignee: Pacesetter AB, Järfälla, Sweden

[21] Appl. No.: 09/194,236
[22] PCT Filed: May 12, 1997
[86] PCT No.: PCT/SE97/00772
§ 371 Date: Jun. 1, 1999
§ 102(e) Date: Jun. 1, 1999
[87] PCT Pub. No.: WO97/45158
PCT Pub. Date: Dec. 4, 1997

[30] Foreign Application Priority Data

May 24, 1996 [SE] Sweden ................................ 9602000

[51] Int. Cl.⁷ .................................................. A61N 1/05
[52] U.S. Cl. .......................................... 607/127; 607/120
[58] Field of Search .................................. 607/120, 121, 607/126, 127, 129, 130; 600/375

[56] References Cited

U.S. PATENT DOCUMENTS 3,974,834  8/1976  Kane .
4,282,885  8/1981  Bisping ................................... 607/127
4,876,109  10/1989 Mayer et al. .
5,003,992  4/1991  Holleman et al. ..................... 607/127
5,447,533  9/1995  Vachon et al. .

FOREIGN PATENT DOCUMENTS 0 422 363  4/1991  European Pat. Off. .

*Primary Examiner*—George R. Evanisko
*Attorney, Agent, or Firm*—Hill & Simpson

[57] ABSTRACT

A device for preventing an anchoring element disposed at the distal end of an implantable electrode cable from coming into contact, during introduction of the cable into a body cavity, with a cavity wall and thereby damaging the cavity wall, as a protection element which either projects beyond the distal tip of the helical anchoring element, or has the distal tip of the helical anchoring element embedded therein. The protection element is composed of a porous, resilient, spongy material which is compressible. The protection element has interstices which are at least partially filled with medication, and the protection element is compressible during affixing of the anchoring element in the heart wall, so as to express the medication from the interstices.

12 Claims, 1 Drawing Sheet

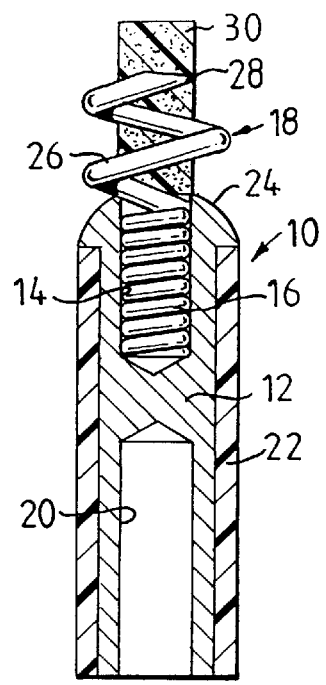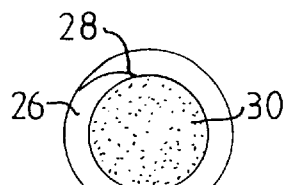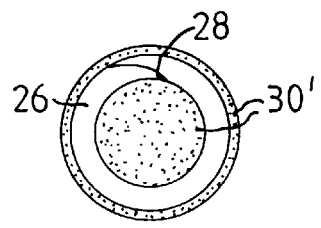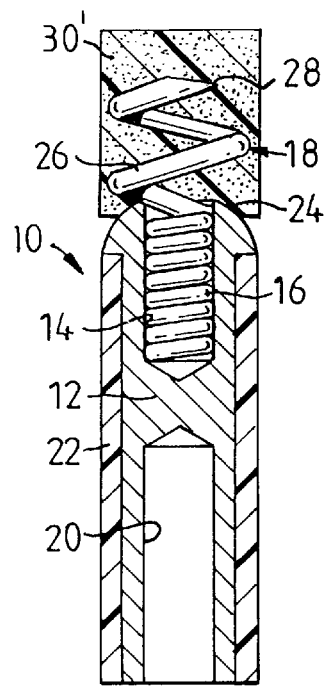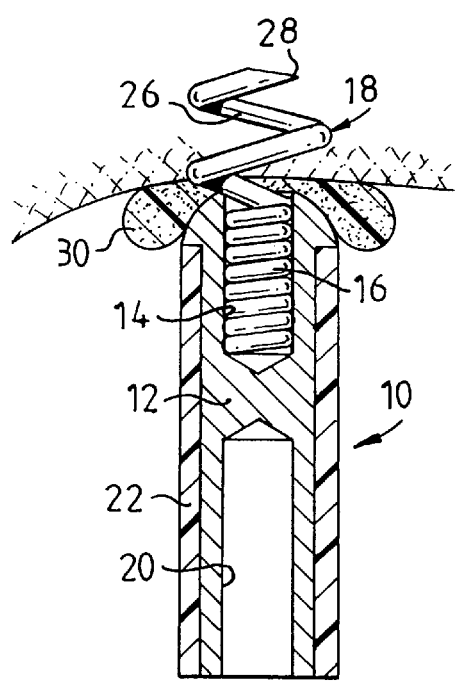

DISTAL END DEVICE FOR AN IMPLANTABLE ELECTRICAL CONDUCTOR AND AN ELECTRICAL CONDUCTOR EQUIPPED WITH SUCH AN END DEVICE

BACKGROUND OF THE INVENTION

1. Field of the Invention

The present invention relates to a device intended for use on the distal end of an actively implantable electrical conductor to prevent a helical anchoring element, projecting from the distal end of the conductor, from damaging the walls of the cavities during implantation of the conductor into body cavities, such as veins and the heart.

2. Description of the Prior Art

Implantable electrical conductors, i.e. electrode cables, intended for connection at their proximal end to a medical device, such as a pacemaker, and whose distal end is to be affixed in a ventricle or atrium of the heart, can, after intravenous introduction into the heart, be passively or actively affixed to the heart wall in order to deliver electrical impulses to heart muscle, thereby causing it to contract, or sense the heart's intrinsic activity in order to control the pacemaker's operating cycle. In passive fixing of the electrode cable, the distal end is usually equipped with small fins or tines to facilitate anchoring this end in the heart wall without penetrating same.

In order to achieve rapid and positive fixing of the distal end of the electrode to the heart wall in implantation of the electrode cable, e.g. when the end of the cable is to have a J shape and press against an atrial wall, active fixation of the cable end to the atrial wall is preferred. For this purpose, the end of the electrode is provided with an anchoring element which can be screwed into wall tissue during implantation. The procedure can be monitored with fluoroscopy to ensure that the cable end is correctly positioned.

A commonly used anchoring element for this purpose has a helical means with a pointed tip. Electrode ends of this kind require active screwing of the anchoring means into the heart wall. In instances in which the helical anchoring element can freely rotate on the end of the electrode cable, the helical screw can be rotated with the aid of a stylet inserted from the proximal end of the electrode cable and engage a polygonal recess in the proximal end of the helical element thereby enabling this helical element to be rotated and affixed to the heart wall with the end of the electrode pressing against that wall.

In order to prevent the pointed end of the helical element from coming into contact with and damaging the walls of veins and the heart during the electrode cable's implantation, the aforementioned freely rotating helical element can be initially retracted into a protective recess at the end of the electrode cable and deployed, with the aid of the stylet, only after the end of the cable has reached the desired fixation site and just before the helical element is screwed in.

In another type of anchoring means for active affixing of the end of the electrode to the heart wall, a non-rotating helical element is attached to the distal end of the electrode and projects freely from same. In this instance the helical element must be provided with some kind of protector to keep the tip of the helical element from damaging the wall of veins and the heart during the electrode cable's implantation. The entire electrode cable, including its sheath, must then be rotated in order to drive the helical element into the heart wall.

Different solutions have been proposed for preventing such fixed, projecting helical element from causing damage during introduction. For example, U.S. Pat. No. 4,876,109 describes a body, covering the helical element, which dissolves in body fluid within a few minutes, whereupon the helical element can be screwed into the heart wall.

Another proposal is shown in U.S. Pat. No. 3,974,834 in which a compressible, bellows-like sleeve on the distal end of the electrode cable protects the helical element during intravenous introduction of cable into the heart and is compressed when pressed against the heart wall, enabling the tip of the helical element to gain a footing before being screwed into the heart wall.

U.S. Pat. No. 5,447,533 shows an active electrode affixing arrangement in which a helical element is kept protectively retracted inside a recess in the distal end of the electrode cable to keep the tip of the helical element from damaging the venous wall during intravenous introduction of the electrode cable introduction into the heart. A medication-dispensing element is arranged to slide coaxially inside the helical element after the helical element has been screwed into the heart wall, towards the heart wall in order to deliver medication to same, e.g. an anti-inflammatory agent.

SUMMARY OF THE INVENTION

An object of the present invention is to provide a simplified end protector, for an anchoring element on the distal end of the electrode cable, which can keep the anchoring element on the distal end of the electrode cable from damaging veins and the heart during introduction as well as deliver medication to the heart wall during and after the anchoring element has been affixed.

According to the invention, this object is achieved in its broadest and simplest form by a device of the aforementioned kind when a body made of a porous, resilient, spongy material is arranged coaxial to the helical anchoring element and whose distal end projects beyond the distal end of the anchoring element, the body being at least partially filled or impregnated with medication and designed to deliver same to endocardium when the means is pressed against the tissue while the anchoring element is being screwed in. The body can be coaxially arranged inside the helical anchoring element or the latter can be at least partially embedded in the material.

The body is preferably made of an elastically deformable material, such as silicone or the like, and can be impregnated with a medication, e.g. an anti-inflammatory agent such as a steroid. In order to reduce the pressure of the elastic, porous body against the heart wall after anchoring, the body's material can also be plastically deformable to some extent.

The invention also relates to an implantable electrode cable provided with an end protector according to the above.

DESCRIPTION OF THE DRAWINGS

FIG. 1 is a sectional, longitudinal view of a distal end portion of an actively affixable electrode cable provided with a combined end detector and medication-dispensing element, according to a first embodiment of the invention, in a relaxed state.

FIG. 2 is an end view of the electrode portion shown in FIG. 1.

FIG. 3 is a sectional, longitudinal view of a distal end portion of an actively affixable electrode cable providing with a combined end protector and medication-dispensing element according to a second embodiment of the invention, in a relaxed state.

FIG. 4 is an end view of the distal end portion shown in FIG. 3.

FIG. 5 is a sectional, longitudinal view of the distal end portion of each of the first and second embodiments respectively shown in FIGS. 1 and 3, in an actively affixed position in a heart wall.

DESCRIPTION OF THE PREFERRED EMBODIMENTS

FIG. 1 shows a distal end section 10 of an electrode cable, with an external diameter of about 2 mm, intended for active fixing to the wall of a cavity in a patient's heart, according to a first embodiment of the invention. The end section 10 has an electrode sleeve 12, which has a distal blind hole 14 to accommodate a fixing part 16 of an anchoring element 18 and a proximal blind hole 20 for receiving a preferably helically wound electrical conductor (not shown). The sleeve 12 and the conductor are surrounded by an insulating outer sheath 22.

The anchoring element 18 also has a fixing part 26, which axially projects about 1.5 mm from the distal electrode end 24 of the sleeve 12, with a helical shape and pointed tip 28 and a diameter of about 0.25 mm.

To keep the tip 28 of the fixing part 26 of the anchoring element 18 from damaging the walls of the vein and heart during intravenous introduction of such an electrode cable, intended for active fixing to the wall of a heart, the fixing part 26 is equipped with a body 30, which projects axially beyond the tip end 28 so this end does not come into hazardous contact with vascular walls. According to the invention, the body 30 is made of a porous, resilient, spongy material which both protects the tip section 28 during introduction of the electrode cable and makes possible local delivery of medication during and after the fixing part 26 is screwed into the heart wall. The material of the body 30 must accordingly be stiff enough to resist the small pressure loading sustained by the body 30 when it impacts with vascular walls during its introductory phase while still being sufficiently resilient and elastic to compress between the heart wall and the distal end of the electrode cable while the fixing part 26 is being screwed into endocardium, as shown in FIG. 5. The helical fixing part 26 can have an outer diameter of about 2.35 mm and an inner diameter of about 1.85 mm. The body 30 can be held in place by friction against the interior of the anchoring element 18, and its proximal end could possibly be mounted on the distal end 24 of the electrode sleeve 12 with some type of adhesive. As shown in FIG. 2, the tip 28 is beveled radially inward so it points in towards the spongy body 30.

The material of the body 30 must also be so porous or spongy that it is capable of impregnation with an appropriate medication for the intended purpose, e.g. an anti-inflammatory agent such as a steroid or some other therapeutic drug.

Silicone is an example of material of the aforementioned kind which meets these specifications and is also biocompatible. Elastic polymer materials, such as Gore-Tex®, could also be used. Such porous, elastic materials can be compressed to about 5–10% of their original thickness. It is not necessary to fill the entire body 30 with medication. In most instances, only part of the body needs to hold medication e.g. the outermost, distal end section. The amount of medication can be about 1 mg.

FIGS. 3 and 4 show a second embodiment of the distal end section of an electrode cable according to the invention. In this embodiment, the fixing part 26 of the anchoring element 18 which projects from the distal end surface 24 is embedded in the porous, spongy body 30' whose external diameter is accordingly equal to or larger than the external diameter of the fixing part 26. After affixing, the body 30' acquires a shape as shown in FIG. 5.

Preferably, the material of the body 30 and the body 30' plastically deformable, at least in part, i.e. so it does not strive to completely resume its original shape after being deformed by compression. Pressure exerted by the elastic material on the heart wall after the body has been compressed could accordingly be reduced, as shown in FIG. 5.

Although modifications and changes may be suggested by those skilled in the art, it is the intention of the inventors to embody within the patent warranted hereon all changes and modifications as reasonably and properly come within the scope of their contribution to the art.

DESCRIPTION OF THE PREFERRED EMBODIMENTS

Although various minor modifications might be suggested by those skilled in the art, it should be understood that my wish to embody within the scope of the patent warranted hereon all such modifications as reasonably and properly come with the scope of my contribution to the art.

What is claimed is:

1. In an implantable electrode cable having a cable sheath with a distal sheath end and containing an electrical conductor terminating in a helical anchoring element projecting from said distal end and adapted for insertion into cardiac tissue for affixing said electrical conductor to cardiac tissue, the improvement comprising:

a protection body composed of porous, resilient, spongy material disposed coaxially with said helical anchoring element beyond said distal sheath end, said protection body having a distal protection body end initially projecting beyond a tip of said anchoring element and being pierceable by said tip, said protection body having interstices at least partially filled with medication and being compressible by said distal sheath end against said cardiac tissue as said anchoring element is inserted into said cardiac tissue to express said medication from said interstices.

2. The improvement of claim 1 wherein said protection body is disposed coaxially inside said helical anchoring element.

3. The improvement of claim 1 wherein said protection body has at least a portion, including said tip, of said helical anchoring element embedded therein.

4. The improvement of claim 1 wherein said protection body is composed of an elastically deformable material.

5. The improvement of claim 4 wherein said elastically deformable material comprises silicone.

6. The improvement of claim 5 wherein said protection body has a non-compressed thickness, and wherein said protection body is compressible to a thickness which is in a range of between 5% and 10% of said non-compressed thickness.

7. The improvement of claim 4 wherein said elastically deformable material at least partially comprises plastically deformable material.

8. The improvement of claim 7 wherein said protection body has a non-compressed thickness, and wherein said protection body is compressible to a thickness which is in a range of between 5% and 10% of said non-compressed thickness.

9. The improvement of claim 1 wherein said medication comprises an anti-inflammatory medication.

10. The improvement of claim 9 wherein said anti-inflammatory medication comprises a steroid.

11. A cardiac lead comprising:

an implantable electrode cable having a cable sheath with a distal sheath end and containing an electrical conductor;

said conductor terminating in a helical anchoring element projecting from said distal sheath end and terminating in a distal tip, said distal tip being adapted for introduction into cardiac tissue for active affixation in said cardiac tissue; and a protection body contained within an interior volume defined by said helical anchoring element and disposed beyond said distal sheath end and initially projecting beyond said distal tip of said helical anchoring element and being pierceable by said distal tip, said protection body being composed of a porous, resilient, spongy material having interstices at least partially filled with medication, said protection body being compressible by said distal sheath end as said anchoring element is inserted into said cardiac tissue to express said medication from said interstices.

12. A cardiac lead comprising:

an implantable electrode cable having a cable sheath with a distal sheath end and containing an electrical conductor;

said conductor terminating in a helical anchoring element projecting from said distal sheath end and terminating in a distal tip said distal tip being adapted for introduction into cardiac tissue for active affixation in said cardiac tissue; and a protection body, disposed beyond said distal sheath end, in which at least a portion, including said distal tip, of said helical anchoring element is initially embedded and being pierceable by said distal tip, said protection body being composed of a porous, resilient, spongy material having interstices at least partially filled with medication, said protection body being compressible by said distal sheath end as said helical anchoring element is inserted into said cardiac tissue for expressing said medication from said interstices.

* * * * *